(12) United States Patent
McGuire (10) Patent No.: US 10,426,567 B2
(45) Date of Patent: Oct. 1, 2019

(54) RETRACTOR WITH IMPROVED LIGHT SOURCE, AND LIGHT SOURCE FOR AN IMPROVED RETRACTOR

(71) Applicant: Clear Surgical Limited, Glasgow (GB)

(72) Inventor: James McGuire, Glasgow (GB)

(73) Assignee: Clear Surgical Limited, Larbert (GB)

( * ) Notice: Subject to any disclaimer, the term of this patent is extended or adjusted under 35 U.S.C. 154(b) by 0 days.

(21) Appl. No.: 15/522,259

(22) PCT Filed: Nov. 12, 2015

(86) PCT No.: PCT/GB2015/053439
§ 371 (c)(1),
(2) Date: Apr. 26, 2017

(87) PCT Pub. No.: WO2016/075474
PCT Pub. Date: May 19, 2016

(65) Prior Publication Data
US 2017/0312045 A1    Nov. 2, 2017

(30) Foreign Application Priority Data

Nov. 12, 2014 (GB) .................................. 1420141.2

(51) Int. Cl.
*A61B 90/35* (2016.01)
*A61B 17/02* (2006.01)
(Continued)

(52) U.S. Cl.
CPC .......... *A61B 90/35* (2016.02); *A61B 17/0206* (2013.01); *A61B 90/30* (2016.02);
(Continued)

(58) Field of Classification Search
CPC ................ A61B 90/35; A61B 17/0206; A61B 2090/0813; A61B 2090/0817;
(Continued)

(56) References Cited

U.S. PATENT DOCUMENTS 3,766,910 A    10/1973    Lake
4,226,228 A    10/1980    Shin et al.
(Continued)

FOREIGN PATENT DOCUMENTS

DE    102006042985 A1    4/2007
EP        0190014 A2    8/1986
(Continued)

OTHER PUBLICATIONS

International Search Report and Written Opinion dated Feb. 23, 2016 from the European Patent Office, 11 pages.

*Primary Examiner* — Pedro Philogene
*Assistant Examiner* — David C Comstock
(74) *Attorney, Agent, or Firm* — Perkins Coie LLP (57) ABSTRACT

The invention provides a retractor having a lighting module which is removeably attached to a paddle of the retractor. The retractor is able to provide improved illumination of a workspace within the body by attaching the light source directly to the paddle. As the light source is removeable from the paddle, it enables the light source to be removed after use and discarded while the retractor can be re-used. Furthermore, as the light source is removeably attached at a distal end of the paddle, the illumination is provided closest to the workspace, regardless of the length of the paddle.

30 Claims, 8 Drawing Sheets

(51) Int. Cl.
*A61B 90/30* (2016.01)
*A61B 17/00* (2006.01)
*A61B 17/28* (2006.01)
*A61B 90/00* (2016.01)

(52) U.S. Cl.
CPC ............... *A61B 2017/00367* (2013.01); *A61B 2017/00473* (2013.01); *A61B 2017/00526* (2013.01); *A61B 2017/00734* (2013.01); *A61B 2017/2837* (2013.01); *A61B 2090/0813* (2016.02); *A61B 2090/0817* (2016.02); *A61B 2090/309* (2016.02)

(58) Field of Classification Search
CPC .... A61B 2090/309; A61B 2017/00367; A61B 2017/00473; A61B 2017/00526; A61B 2017/00734; A61B 2017/2837
USPC .......................................... 600/212, 223, 245
See application file for complete search history.

(56) References Cited

U.S. PATENT DOCUMENTS

| | | | |
|---|---|---|---|
| 4,502,485 A | 3/1985 | Burgin | |
| 4,562,832 A | 1/1986 | Wilder et al. | |
| 5,005,108 A | 4/1991 | Pristash et al. | |
| 5,035,232 A * | 7/1991 | Lutze | A61B 17/02 600/213 |
| 5,503,617 A | 4/1996 | Jako | |
| 5,569,300 A | 10/1996 | Redmon | |
| 5,871,493 A | 2/1999 | Sjostrom et al. | |
| 5,944,736 A | 8/1999 | Taylor et al. | |
| 6,080,105 A | 7/2000 | Spears | |
| 6,185,356 B1 | 2/2001 | Parker et al. | |
| 6,224,545 B1 | 5/2001 | Cocchia et al. | |
| 6,504,985 B2 | 1/2003 | Parker et al. | |
| 6,554,768 B1 | 4/2003 | Leonard | |
| 6,602,189 B1 | 8/2003 | Bennetti et al. | |
| 7,686,492 B2 * | 3/2010 | Vayser | A61B 1/0623 362/572 |
| 8,088,066 B2 | 1/2012 | Grey et al. | |
| 8,137,284 B2 | 3/2012 | Miles et al. | |
| 8,435,175 B2 | 5/2013 | McMahon et al. | |
| 2003/0060686 A1 | 3/2003 | Taylor et al. | |
| 2003/0095781 A1 | 5/2003 | Williams | |
| 2004/0024291 A1 | 2/2004 | Zinkel | |
| 2004/0242971 A1 | 12/2004 | Holland et al. | |
| 2005/0096646 A1 | 5/2005 | Wellman et al. | |
| 2005/0154263 A1 | 7/2005 | Nady | |
| 2006/0217596 A1 | 9/2006 | Williams | |
| 2007/0060795 A1 | 3/2007 | Vayser et al. | |
| 2007/0244353 A1 | 10/2007 | Larsen | |
| 2007/0293729 A1 * | 12/2007 | Grey | A61B 1/00105 600/212 |
| 2008/0108877 A1 | 5/2008 | Bayat | |
| 2008/0114207 A1 | 5/2008 | Krupa et al. | |
| 2008/0234549 A1 | 9/2008 | Geist et al. | |
| 2008/0269565 A1 | 10/2008 | McMahon et al. | |
| 2009/0018399 A1 | 1/2009 | Martinelli et al. | |
| 2009/0187078 A1 | 7/2009 | Dunlop | |
| 2009/0203969 A1 | 8/2009 | Cohen et al. | |
| 2010/0317928 A1 * | 12/2010 | Subramaniam | A61B 17/0206 600/245 |
| 2011/0144439 A1 | 6/2011 | Miles et al. | |
| 2012/0041268 A1 * | 2/2012 | Grey | A61B 1/00105 600/199 |
| 2012/0116170 A1 | 5/2012 | Vayser et al. | |
| 2012/0149992 A1 | 6/2012 | Duggal et al. | |
| 2012/0209076 A2 | 8/2012 | Hahn et al. | |
| 2012/0209080 A1 | 8/2012 | Grey et al. | |
| 2012/0238822 A1 | 9/2012 | Miles et al. | |
| 2014/0323811 A1 * | 10/2014 | DeSantis | A61B 1/06 600/213 |
| 2015/0265320 A1 * | 9/2015 | Hynes | A61B 17/7074 606/279 |

FOREIGN PATENT DOCUMENTS

| | | |
|---|---|---|
| GB | 1381387 | 1/1975 |
| GB | 2481585 A | 1/2012 |
| JP | 2008194086 A | 8/2008 |
| WO | 2005102177 A1 | 11/2005 |
| WO | 2009037498 A2 | 3/2009 |

* cited by examiner

RETRACTOR WITH IMPROVED LIGHT SOURCE, AND LIGHT SOURCE FOR AN IMPROVED RETRACTOR

The present invention relates to the field of surgical retractors. More specifically, the present invention concerns improvements to light sources for retractors that provide improved illumination and utility. In a particular embodiment of the invention there is provided a retractor having a lighting module which is removeably attached to a paddle of the retractor, and in another embodiment of the invention there is provided a lighting module which is removeably attachable to a paddle of a retractor.

BACKGROUND TO THE INVENTION

A retractor is a surgical instrument that is used to separate the edges of a surgical incision or wound, holding back underlying tissues and organs so that body parts under the incision may be accessed. Retractors are available in many different shapes, sizes and styles.

A typical retractor comprises a scissor-type arrangement of two elongated arms mechanically connected by a pivot. At the distal end (in use) of each elongated arm is a paddle (or blade) and at the proximal end (in use) of each elongated arm is a handle; separation of the paddles being controlled by manipulation of the handles. Unlike scissors, the handles are brought together to separate the paddles. A ratchet or similar mechanism is used to hold the paddles in a separated position.

During surgery, when the retractor is employed to hold open (for example) a surgical incision, a separate light source is usually required to illuminate the workspace created. Typically a surgeon may use a head-mounted light or other external light source. However, when the incision and/or workspace is deep within the body, such light sources are unreliable and often provide poor illumination. Furthermore, shadows can be cast within the workspace which make it hard to operate effectively.

Figure 1:
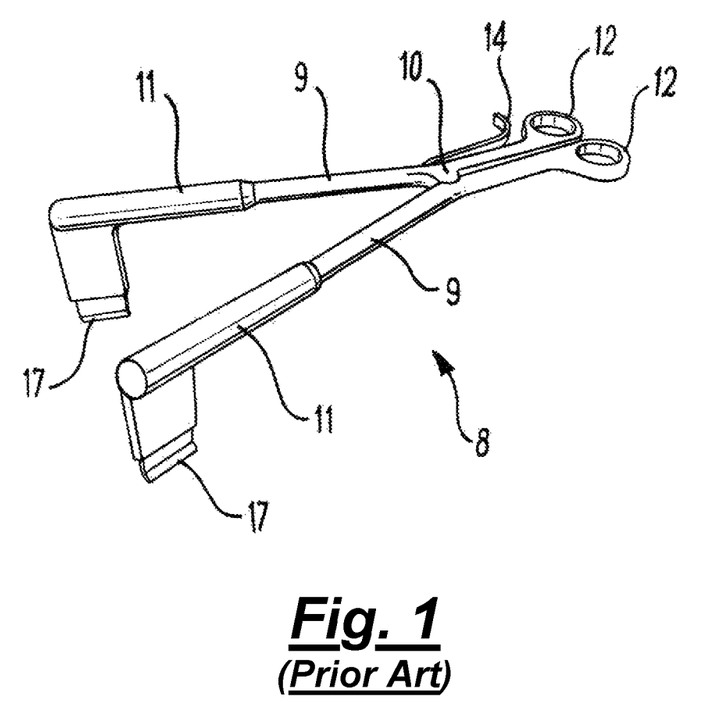
FIG. 1 is a perspective view of a prior art surgical retractor comprising an integrated light source.

To remedy this problem, WO2009/037498 (FIG. 2a of which is reproduced herein as FIG. 1) discloses a retractor with an integrated light source. The retractor 8 is of a type comprising two elongated arms 9 mechanically connected by a pivot 10. At the distal end of each elongated arm 9 is located a paddle assembly 11, the separation of the paddle assemblies 11 being controlled through the manual manipulation of handles 12 located at the proximal end of the elongated arms 9. The paddle assemblies 11 comprise independent units which snap fit onto the distal ends of the elongated arms 9. Each paddle assembly 11 comprises an hermetically sealed unit which encloses a light source and a corresponding power source. The paddle 17 can be adjusted so as to allow a surgeon to alter the size of the retractor 8 depending on the depth of the incision (or in other words the amount of skin, fat and muscle that has to be retracted) by pulling the paddle 17 out of, or pushing the paddle 17 into, the casing.

This retractor provides a source of light inside the retracted tissue area to illuminate the tissue of interest and/or workspace without obstructing the view or hindering the manual dexterity of the surgeon, or indeed requiring additional manipulation of a separate light source (or light sources), whether by the surgeon or by his or her assistants.

Notwithstanding the improvements over conventional retractors and illumination practices enabled by the teachings of WO2009/037498, it is an object of at least one aspect of the present invention to provide a retractor that provides further advantages over conventional retractors, and obviates or mitigates one or more disadvantages of same.

Further aims and objects of the invention will become apparent from reading the following description.

SUMMARY OF THE INVENTION

According to a first aspect of the invention, there is provided a retractor comprising at least one paddle and at least one light source, wherein the at least one light source is removeably attached to the at least one paddle.

The above invention provides a retractor which is able to provide improved illumination of a workspace within the body by way of a light source which is attached to the paddle (or blade) which creates the workspace. As the light source is removeable from the paddle, it enables the light source to be removed after use and discarded while the retractor—which may be comprised of surgical steel for ease of sterilisation—can be re-used.

Preferably, the at least one light source is removeably attached to or towards a distal end of the paddle. By removeably attaching the light source to or towards a distal end of the paddle (that is, the end of the paddle which is inserted into the body) the illumination is provided closest to the workspace. This is particularly advantageous if the paddle is elongate because the workspace will be deep within the body and otherwise difficult to illuminate. The retractor may therefore comprise a paddle which may be longer, and optionally may be significantly longer, than the lighting module. For example, the length of the paddle may be 2 to 10 times the length of the lighting module.

Note that the present invention applies not only to retractors of a scissor-type arrangement such as discussed in the background to the invention and in preferred embodiments, but to retractors comprising a single paddle which may for example be held manually, clamped in place, or manipulated by a robotic arm.

Accordingly, the retractor may comprise a single paddle and a single light source removeably attached to the paddle. Such a retractor may be of the Farabeuf type. Alternatively, the retractor may comprise two paddles arranged at the ends of corresponding arms mechanically connected by a pivot which permits the retractor to be moved between a closed and an open position, a light source removeably attached to a distal end of each paddle. Such a retractor may be of the Williams type.

Preferably, the retractor comprises a retention feature by which the at least one light source is removeably attached to the at least one paddle. Preferably, the retention feature comprises a male runner and a female runner which receives the male runner. Preferably the male runner is disposed on the light source and the female runner is disposed on the paddle. Advantageously, the male runner comprises an end face which abuts a corresponding end face of the female runner. This may prevent unwanted movement of the light source.

Additionally, or alternatively, the retention feature may comprise one or more male pips and one or more female slots which receive the one or more male pips. Optionally, or alternatively, the retention feature may comprise a recess in the paddle which receives the light source. Such features may also prevent unwanted movement of the light source.

The retention feature may comprise one or more studs, corresponding ridges and channels, plugs and sockets, components of which may be disposed on either of the paddle and the light source.

Preferably, the light source comprises a lighting module having a first housing portion and a second housing portion attached to the first housing portion. Preferably, the second housing portion is welded to the first housing portion so as to form a hermetic seal.

Between the first housing portion and the second housing portion there is preferably located one or more LEDs. Preferably the LEDs are side-emitting LEDs. Preferably the first housing portion is configured, arranged or adapted to function as a waveguide which received light from the one or more LEDs. Preferably the first housing portion comprises a diffusing surface which enables the first housing portion to function as a light guide panel. The diffusing surface may comprise etching, moulding or printing on an internal face of the first housing portion. The first housing portion may comprise recesses which receive the one or more LEDs to enable coupling of light into the first housing portion.

Optionally the first housing portion comprises a first and a second section wherein the first section has a thickness that is greater than that of the second section. Most preferably the first section is configured to align with the location of the one or more LEDs to form a light exit surface at the interface between the first and second sections of the first housing portion. As a result, during use, the majority of the light emitted by the LEDs exits the lighting module via the light exit surface, rather than being guided through the first housing portion and into the second section. This is particularly true when the LEDs are side-emitting LEDs. It should be noted that some of light from the side-emitting LEDs may still propagate into the second section. The light exit surface also provides an operator with a finger grab facility that can be employed to assist in the removal of the lighting module.

Optionally, the lighting module comprises a switch configured to selectively provide electrical power to the one or more LEDs. Preferably, the switch comprises a press switch actuable via the first housing portion. Optionally, the first housing portion comprises a dome feature aligned with the switch which may be depressed to actuate the switch. Alternatively, the switch is configured to actuate automatically when the lighting module is attached to the paddle. For example, the switch may be located on a surface of the lighting module which contacts a corresponding surface of the paddle.

In a preferred embodiment of the first aspect of the invention, the retractor comprises two paddles arranged at the ends of corresponding arms mechanically connected by a pivot which permits the retractor to be moved between a closed and an open position by handles opposing the paddles, a light source removeably attached to a distal end of each paddle by means of a retention feature comprising a male runner disposed on the light source and a corresponding female runner disposed on the paddle which receives the male runner, each light source comprising one or more side-emitting LEDs and a waveguide arranged and/or adapted to provide diffuse illumination of a workspace between the paddles.

According to a second aspect of the invention there is provided a retractor light source, wherein the retractor light source is removeably attachable to a distal end of a paddle of a retractor.

Embodiments of the second aspect of the invention may comprise features corresponding to the preferred or optional features of the first aspect of the invention or vice versa.

According to a third aspect of the invention there is provided a kit of parts comprising at least one retractor comprising at least one paddle adapted, arranged or configured to receive a light source at a distal end, and at least one light source adapted, arranged or configured for removeable attachment to the distal end of the paddle of the at least one retractor.

Preferably, the kit comprises a plurality of retractors and a plurality of light sources. The light sources may comprise retractor light sources according to the second aspect.

Embodiments of the third aspect of the invention may comprise features corresponding to the preferred or optional features of the first or second aspects of the invention or vice versa.

According to further aspects of the invention, there is provided a retractor or a light source for a retractor substantially as herein described with reference to FIGS. 2 to 9 of the appended drawings.

BRIEF DESCRIPTION OF THE DRAWINGS

There will now be described, by way of example only, various embodiments of aspects of the invention with reference to the drawings, of which:

FIG. 2 shows in (a) side elevation, (b) front elevation and (c) isometric view a retractor paddle assembly according to an embodiment of the present invention;

FIG. 4 illustrates (a) the retractor paddle assembly of FIGS. 2 and 3 in (b) sectional view and (c), (d) and (e) enlarged sectional views, showing how the lighting module is received and retained on the paddle;

FIG. 6 illustrates in (a) exploded view and in (b) and (c) enlarged sectional views the lighting module assembly showing interior components and arrangements;

FIG. 12 shows in (a) an isometric view and (b) a side elevation a retractor paddle according to an alternative embodiment of the present invention.

DETAILED DESCRIPTION OF PREFERRED EMBODIMENTS

An embodiment of the present invention is illustrated in FIGS. 2 to 7 and provides many and significant advantages over the prior art.

Figure 2A:
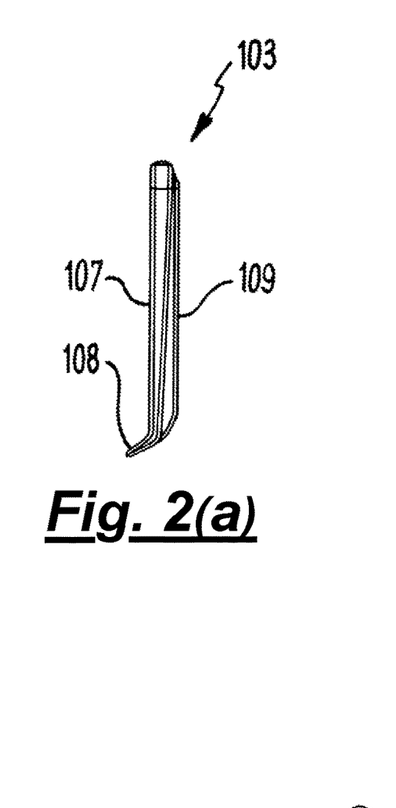
Figure 2B:
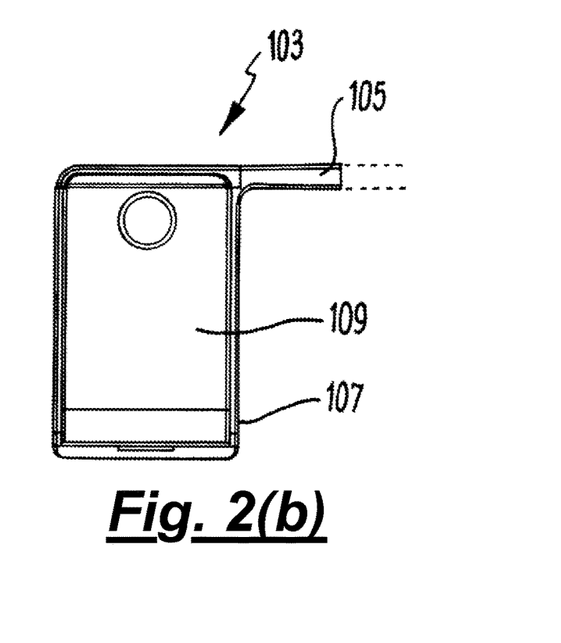
Figure 2C:
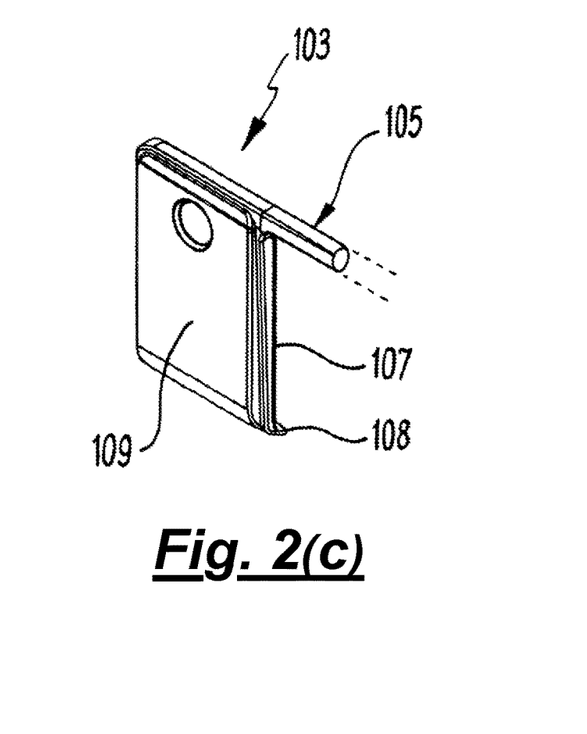

FIG. 2 illustrates a retractor paddle assembly 103 located at the end of an elongate arm 105 of a retractor 101. The paddle assembly 103 comprises a paddle 107 and a lighting module 109 which is removeably attached to an inner face of the paddle 107. The outer face of the paddle 107, in use, engages the tissue and/or organs to be held away from the workspace and a lip 108 at the distal end of the paddle 107 assists in this regard. The lighting module 109 is described in further detail below with reference to FIG. 6.

As envisaged above in the summary of the invention, the lighting module 109 is attached to the distal end of the paddle 107. Although in this embodiment the lighting module 109 is of comparable size to the paddle 107, the relative location of the lighting module 109 may be more readily appreciated in the alternative embodiment shown in FIG. 8 and described further below. In any case, the location of the lighting module 109 on the paddle 107 is such that when in use the lighting module is able to illuminate the workspace because it will be inherently proximal to the workspace. Note that the lighting module is self-contained and wholly located on the paddle.

Figure 3:
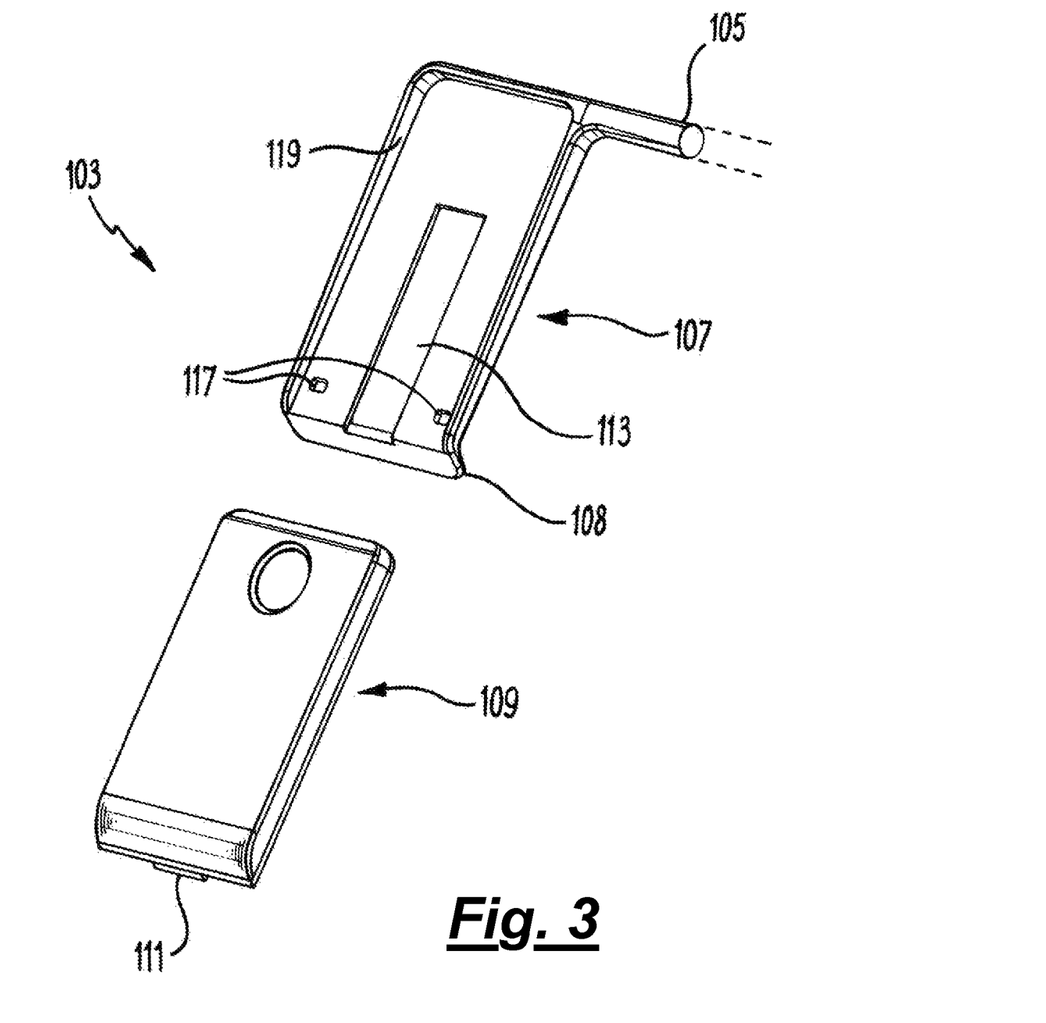
FIG. 3 shows in perspective view the retractor paddle assembly of FIG. 2 in a disassembled configuration with the paddle and light module separated.
Figure 4A:
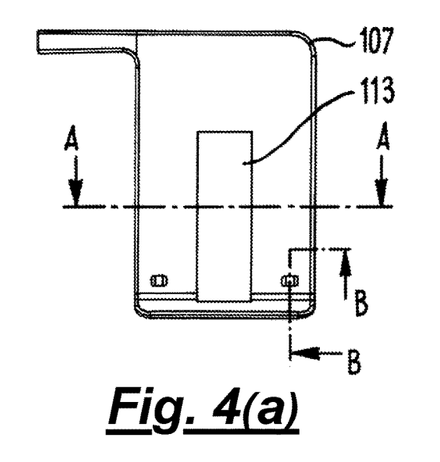
Figure 4B:
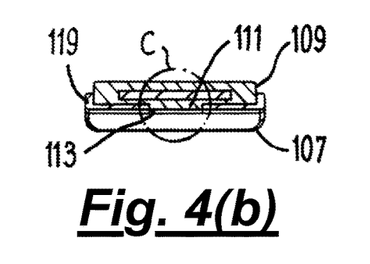
Figure 4C:
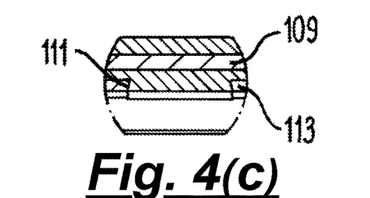
Figure 4D:
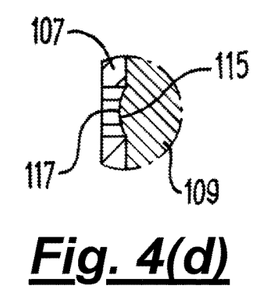
Figure 4E:
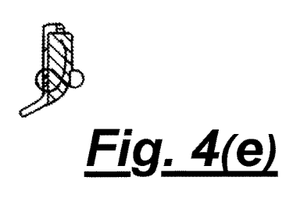

FIG. 3 shows the above-described retractor paddle assembly 103 in a disassembled configuration which may be prior to attachment of the lighting module 109 to the retractor paddle 107, or after detachment of the lighting module 109 from the retractor paddle 107. The lighting module 109 is attached to the retractor paddle 107 as follows. The lighting module 109 in this embodiment comprises an elongate male runner 111 located on a rear surface of the lighting module 111, which is received in a corresponding elongate female runner 113 on a front surface of the paddle 107. The upper end of the male runner 111 (which can be seen more clearly in FIGS. 4 and 5, described below) is aligned with the lower end of the female runner 113, inserted into the female runner 113, and advanced until it abuts a corresponding upper end face of the female runner 113. This arrangement prevents the lighting module 109 from being pushed upwards off, or away from the distal end of, the paddle 107 when inserted into an incision or wound in a body.

Further retention is provided by the provision of female slots 117 on the front surface of the paddle 107 which receive corresponding male pips 115 (not shown, but which can be seen in FIGS. 4 and 5, described below). This prevents the lighting module 109 from being easily pushed off of the paddle 107 for example when inserting a surgical instrument into the workspace which might brush or knock the lighting module 109. Note that the paddle 107 comprises a recess 119 which also receives the lighting module 109 and thereby limits lateral movement which might otherwise dislodge the lighting module 109.

FIG. 4 illustrates in more detail the engagement between the lighting module 109 and the paddle 107. FIG. 4(a) shows the paddle 107 from behind, with the female runner 113 and female slots 117 on the opposing face visible for reference. FIG. 4(b) shows an enlarged view through section A-A, wherein the lighting module 109 is attached to the paddle 107 with male runner 111 engaged within female runner 113, and the lighting module 109 located within the recess 119. FIG. 4(c) shows in further detail the diverging bevelled cross-section of the female runner 113 and the corresponding converging bevelled cross-section of the male runner 111 which serves as a further retention feature holding the lighting module 109 onto the paddle 107. FIG. 4(d) shows an enlargement of section B-B of FIG. 4(e) in which the male pip 115 is located in the corresponding female slot 117. The male pip 115 has a domed surface which acts as a lead in then snaps into place when aligned with the slot 117.

Figure 5:
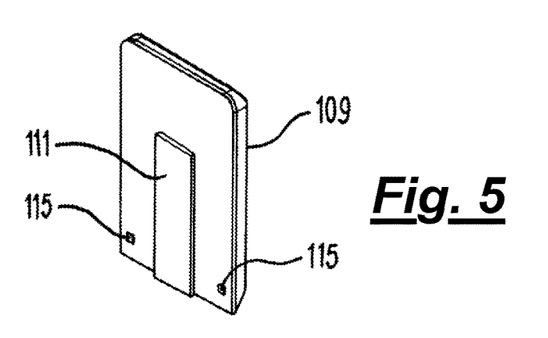
FIG. 5 illustrates the rear surface of the lighting module showing retention features comprised thereon.

As referred to above, FIG. 5 shows further detail of the back face of the lighting module 109, clearly showing the male runner 111 and the male pips 115 which cooperate with the female runner 113 and female slots 117 of the paddle 107, respectively.

Figure 6A:
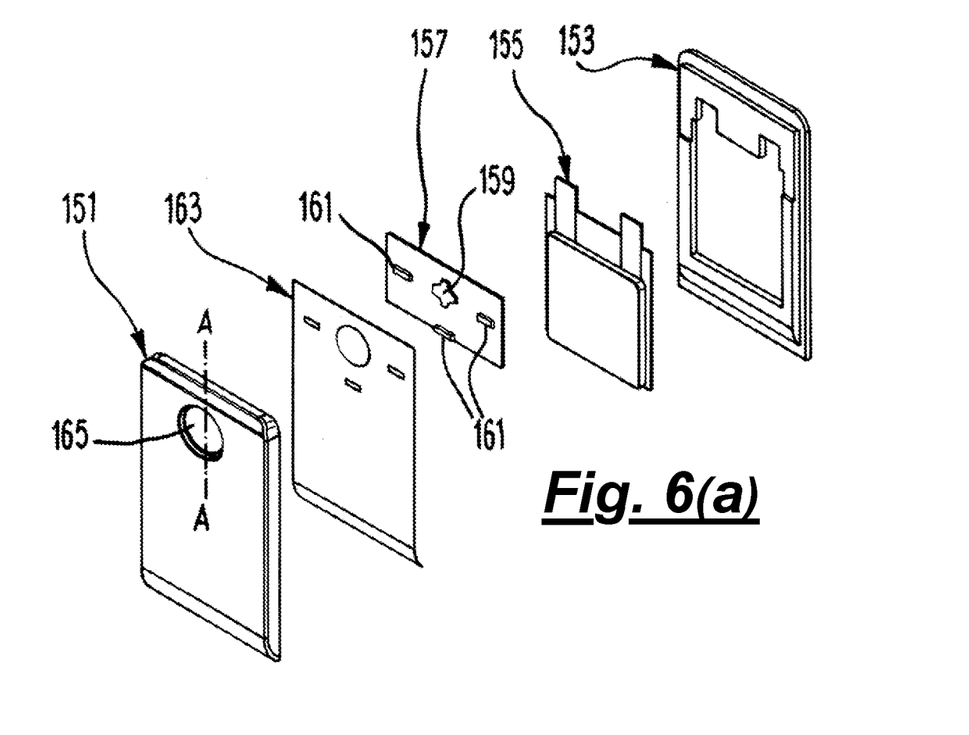

Further detail of the lighting module 109 is illustrated in the exploded view of FIG. 6(a). The lighting module 109 can be seen to comprise a front piece 151 and a rear piece 153, which contain the other components of the lighting module 109. The front piece 151 and rear piece 153 may be welded together to form a hermetic seal to avoid contamination.

Figure 6B:
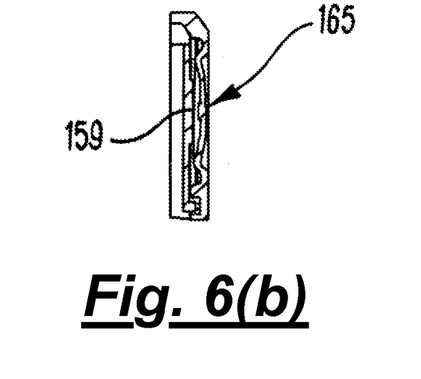
Figure 6C:
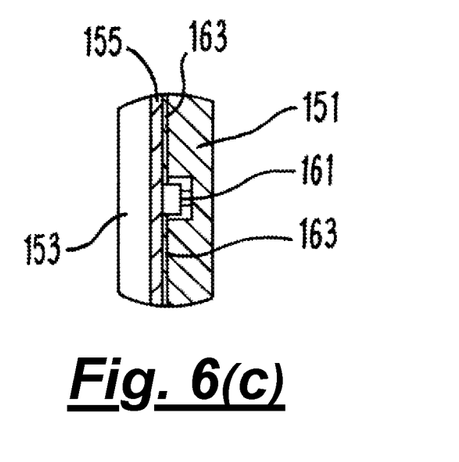

Sandwiched between the front piece 151 and rear piece 153 are a battery 155, a printed circuit board 157 bearing a dome switch 159 and three side-emitting LEDs 161, and a reflector 163 with apertures corresponding to the dome switch 159 and LEDs 161 which protrude there through. The front piece 151 is provided with a dome feature 165 aligned with the dome switch 159, as shown in FIG. 6(b), and the dome feature 165 can be pressed to actuate the dome switch 159 to switch the LEDs 161 on and off as required. As shown in FIG. 6(c) each LED 161 is received in a corresponding recess of the front piece 151, and the front piece then acts as a waveguide. A light scattering pattern is etched (or may be moulded or printed) onto the internal face of the front piece 151 to create a light guide panel for relatively diffuse illumination of the workspace.

Figure 7:
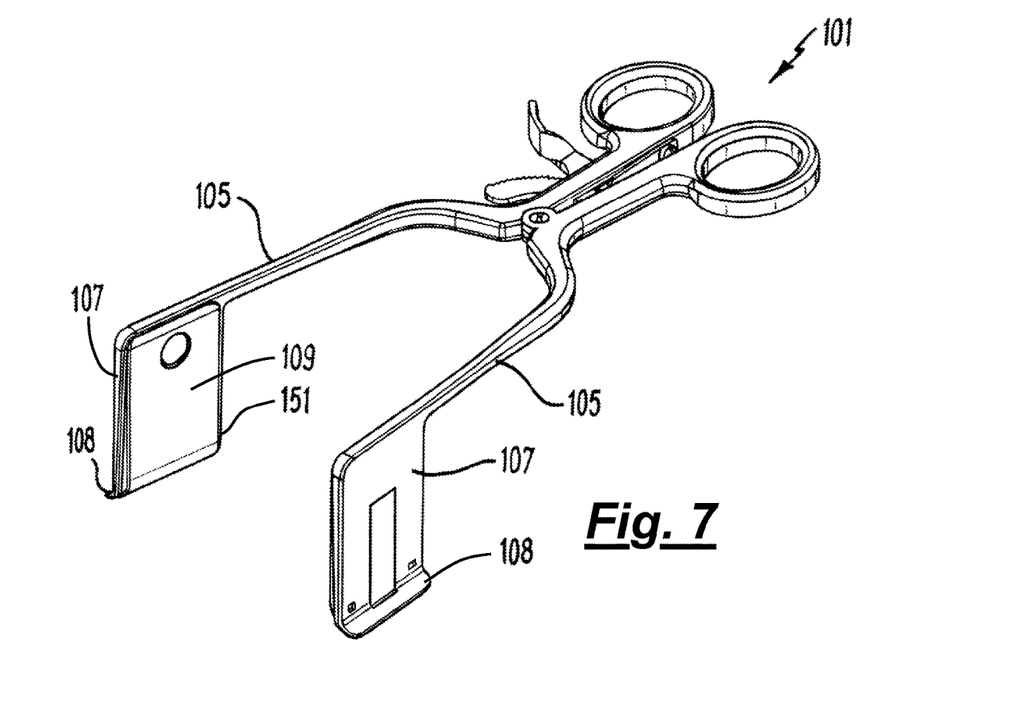
FIG. 7 illustrates a surgical retractor comprising paddle assemblies with removeable lighting modules in accordance with an embodiment of the present invention.

FIG. 7 illustrates a scissor-type or "Williams" retractor 101 comprising a pair of pivotally attached elongate arms 105; at the end of each arm is located a paddle 107 and a lighting module 109 attached to the paddle in the manner described above with reference to FIGS. 2 to 6. The lighting modules 109 are attached to respective paddles 107 prior to use and illumination switched on by pressing the dome feature 165 to actuate the dome switch 159. The light guide panel provided by the front piece 151 then provides illumination to the workspace created by the retractor when used to separate and hold apart tissues and/or organs.

Figure 8:
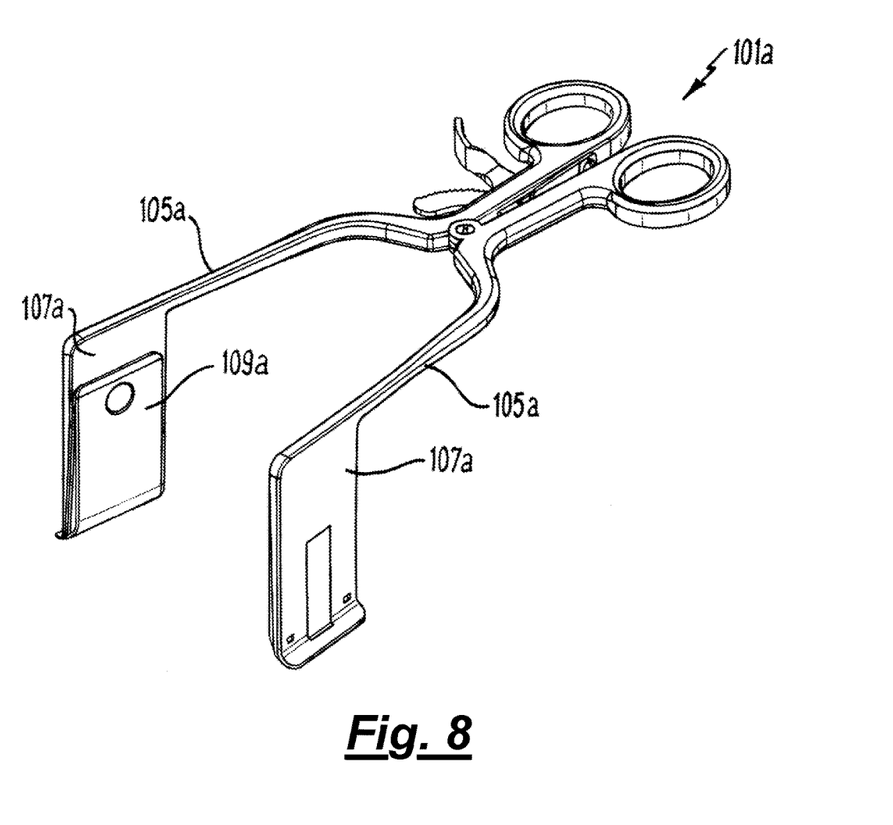
FIG. 8 illustrates a surgical retractor comprising paddle assemblies with removeable lighting module in accordance with an alternative embodiment of the present invention, in which the paddles are longer than those of the surgical retractor illustrated in FIG. 7.

A particular advantage of the use of a lighting module which is removeably attached to the paddles is that different sizes, shapes and types of retractor may be used to suit the particular application. For example, FIG. 8 shows a scissor-type or "Williams" retractor 101a similar to that shown in FIG. 7, however employing longer paddles 107a. As can be seen, the lighting modules 109a are attached to the paddles 107a in a similar manner. However, as the paddles 107a are longer than the paddles 107 shown in FIG. 7, the lighting modules 109a are more obviously located toward the distal end of the paddles 107a. In use this means that the light provided by the lighting modules 109a provides effective illumination of the workspace regardless of the increased length of the paddles.

A retractor kit is envisaged in which one or more retractors of different size, shape and type, and particularly of different paddle length, are provided, with one or more lighting modules which can be attached to any of the retractors by virtue of a common retention feature.

Figure 9:
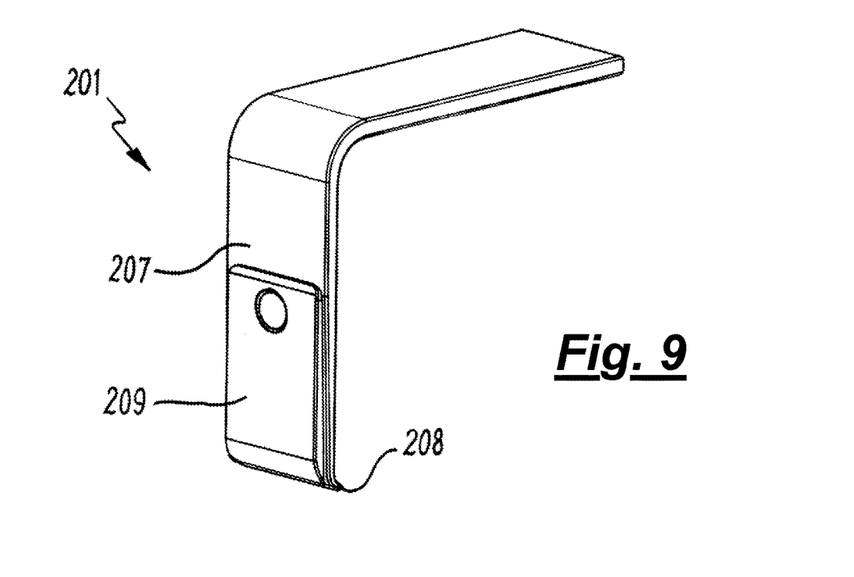
FIG. 9 illustrates an alternative surgical retractor comprising a paddle assembly with a removeable lighting module.

FIG. 9 illustrates an alternative retractor 201 of the "Farabeuf" type which comprises a single paddle 207 which is yet longer than the paddle 107a shown in FIG. 8. Again, it can be seen that the lighting module 209 is located at a distal end of the paddle 207 and therefore provides effective illumination of a correspondingly deeper workspace than that accessed by the retractors 101, 101a of FIGS. 7 and 8 respectively.

Figure 10:
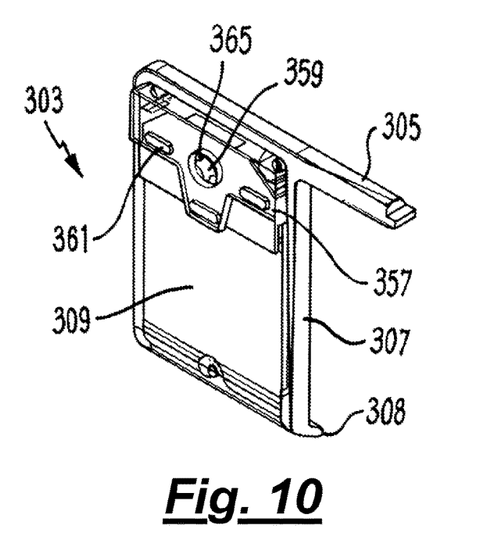
FIG. 10 shows an isometric view of a retractor paddle assembly according to an alternative embodiment of the present invention.

FIG. 10 illustrates an alternative retractor paddle assembly 303 located at the end of an elongate arm 305 of a retractor. The paddle assembly 303 again comprises a paddle 307 and a lighting module 309 which is removeably attached to an inner face of the paddle 307. The outer face of the paddle 307, in use, again engages the tissue and/or organs to be held away from the workspace and a lip 308 at the distal end of the paddle 307 assists in this regard. The main difference within the retractor paddle assembly 303 when compared to those described above relates to the form of the lighting module 309. For ease of understanding a side view of the lighting module 309 is presented within FIG. 11.

Figure 11:
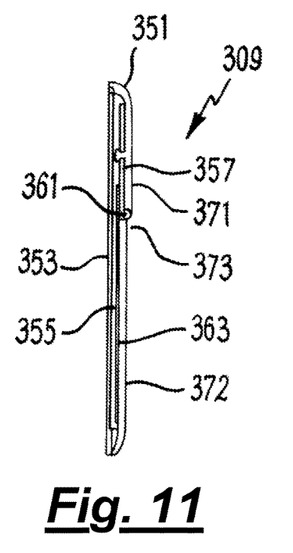
FIG. 11 shows side view the light module of the retractor paddle assembly of FIG. 10.

The lighting module 309 can be seen to comprise a front piece 351 and a rear piece 353, which contain the other components of the lighting module 309. The front piece 351 and rear piece 353 may again be welded together to form a hermetic seal to avoid contamination.

Sandwiched between the front piece 351 and rear piece 353 is the battery 355; the printed circuit board 357 which again bears the dome switch 359 and three side-emitting LEDs 361; and a reflector 363 again having apertures corresponding to the dome switch 159 and LEDs 161 which protrude there through.

In this embodiment, the front piece 351 can be seen to comprise a first 371 and a second section 372 wherein the first section 371 has a thickness that is greater than that of the second section 372. The first section 371 is configured such that it aligns with the location of the printed circuit board 357 and is provided with a dome feature 365 that aligns with the dome switch 359, as shown in FIG. 10.

As can be seen from FIGS. 10 and 11 this arrangement allows the three side-emitting LEDs 361 protrude from the PCB by an amount that allows them to extend beyond the thickness of the second section 372 of the front piece 351 i.e. the three side-emitting LEDs 361 sit proud of the second section 372 of the front piece 351 and the reflector 363. This arrangement results in a light exit surface 373 effectively being formed at the interface between the first 371 and second sections 372 of the front piece 351.

As a result, during use, the majority of the light emitted by the three side-emitting LEDs 361 exits the lighting module 309 via the light exit surface 373, rather than being guided through the front piece and into the second section 372. It should be noted that some of light from the three side-emitting LEDs 361 does however propagate into the second section 372, this mainly be done for cosmetic effects.

The use of the lighting module 309 results in more light propagates directly into the workspace as compared to those embodiments as described above while also helping to protect against upward glare be experience by an operator. The light exit surface 373 also provides an operator with a finger grab facility that can be employed to assist in the removal of the lighting module 309.

Figure 12A:
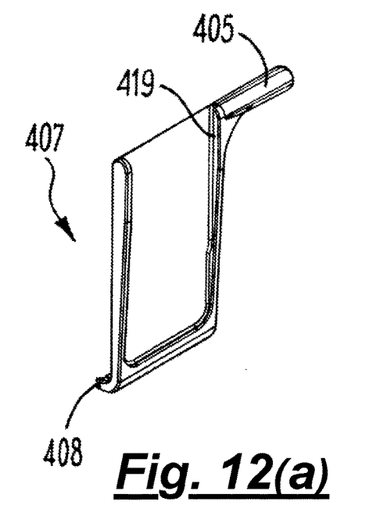
Figure 12B:
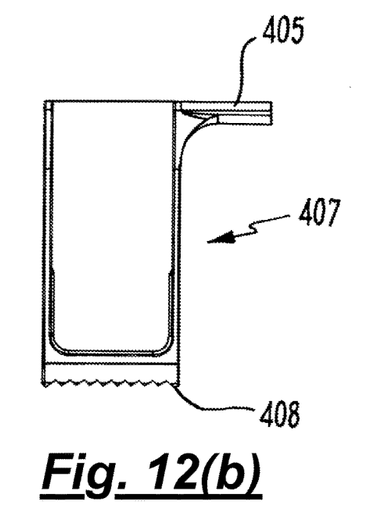

FIG. 12 presents an isometric view and a side elevation a retractor paddle 407 according to an alternative embodiment of the present invention. The retractor paddle 407 is particularly suited for use with the lighting module 309 described above with reference to FIGS. 10 and 11. In this embodiment the recess 419 of the retractor paddle 407 is arranged such that its open end is opposite the distal end of the retractor paddle 407 i.e. the lighting module 309 is inserted into the retractor paddle 407 from the side of the retractor arm 405. Additional retention means, as described above may also be incorporated into the retractor paddle 403. The lip 408 of the retractor paddle 407 can be seen to comprise a serrated edge which is found to assists in the formation of the workspace.

As envisaged above in the summary of the invention, the lighting module 309 is attached to the distal end of the paddle 407. Although in this embodiment the lighting module 309 is of comparable size to the paddle 407 this need not necessarily be the case. It is however again noted that the lighting module 309 is self-contained and wholly located on the paddle 407.

After use (of any of the retractor embodiments described herein) the lighting module or modules may be removed from the respective paddle or paddles and discarded, and the retractor—which may be comprised of surgical steel for example—can be easily sterilised prior to subsequent use at which time a new lighting module or new lighting modules can be attached.

Note that the retention arrangement described herein is but one example of a suitable retention arrangement to removeably attach a lighting module to a paddle in accordance with the present invention. For example, one or more of the described retention features above may be omitted without departing from the scope of the invention defined by the claims. Likewise, male and female components such as the runners of the lighting module and paddle, respectively, may be alternated for their opposite gender. For example, the male runner may be located on the paddle and the female runner on the lighting module. Alternative retention features such as studs, ridges along side edges of the lighting module and corresponding channels in the paddle (or vice versa), plugs and sockets, or other fastening means may be employed in the alternative or indeed in addition to other retention features.

The dome switch of the lighting module may be replaced with any other kind of user actuable switch, or indeed may be omitted in favour of a switch which is automatically actuated when the lighting module is attached to the paddle. For example, a switch may be located at an end face of the male runner of the lighting module which is then activated when the male runner abuts an end face of the corresponding female runner. In this way when the lighting module is attached the light source switches on and when the lighting module is detached the light source switches off. A proximity switch may provide similar functionality.

In the examples above the light source is exemplified by way of three side-emitting LEDs such as described with reference to FIG. 6 above. However, any number of any type of LEDs may be employed, and indeed it will be recognised that any suitable light source may be employed. For example, a planar LED, LED array or OLED panel may be employed to provide uniform illumination without the need for a waveguide (although a waveguide may still be used). In fact, the light source can be shaped or otherwise configured or arranged to provide a desired illumination profile. The illumination may be of any desired colour dependent on application and it is envisaged that repeated presses of a button (such as the dome switch) might permit cycling through a range of useful colours.

As compared to the retractor of WO2009/037498 discussed in the background to the invention, the retractor of the present invention provides a number of advantages. In the prior art retractor, the paddles can be enlarged but this has the effect of increasing the distance between the light sources and the workspace—whereas in the present invention larger paddles can be adopted but the light sources remain proximal to the workspace by virtue of attachment to the ends of the paddles. Furthermore, the light sources can be removed from the paddles which allows for greater flexibility in the choice of materials for the body of the retractor—for example surgical steel can be used which reduces costs not only in terms of manufacture, but also in terms of sterilisation as the light sources can be removed and disposed of leaving a device comprised solely of surgical steel. In addition, the legs of such retractors can be deformed manually to accommodate wider—or indeed narrower—incisions, apertures or wounds—not achievable using the retractor of WO2009/037498.

The invention provides a retractor having a lighting module which is removeably attached to a paddle of the retractor. The retractor is able to provide improved illumination of a workspace within the body by attaching the light source directly to the paddle. As the light source is removeable from the paddle, it enables the light source to be removed after use and discarded while the retractor can be re-used. Furthermore, as the light source is removeably attached at a distal end of the paddle, the illumination is provided closest to the workspace, regardless of the length of the paddle.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

Various modifications may be made within the scope of the invention as herein intended, and embodiments of the invention may include combinations of features other than those expressly claimed.

The invention claimed is:

1. A retractor comprising:
at least one paddle; and
at least one light source, wherein the at least one light source is removeably attached to the at least one paddle, the light source comprising:
a lighting module having a first housing portion, a second housing portion attached to the first housing portion, and one or more LEDs located between the first housing portion the second housing portion, the first housing portion comprising:
a first section and a second section wherein the first section has a thickness that is greater than that of the second section and the first section is aligned with the location of the one or more LEDs to form a light exit surface at the interface between the first section and second section.

2. The retractor of claim 1, wherein the at least one light source is removeably attached to or towards a distal end of the paddle.

3. The retractor of claim 1, wherein the at least one paddle is longer than the at least one light source.

4. The retractor of claim 1, comprising a single paddle and a single light source removeably attached to the paddle.

5. The retractor of claim 4, wherein the retractor is of the Farabeuf type.

6. The retractor of claim 1, comprising two paddles arranged at the ends of corresponding arms mechanically connected by a pivot which permits the retractor to be moved between a closed and an open position, wherein a light source is removeably attached to a distal end of each paddle.

7. The retractor of claim 6, wherein the retractor is of the Williams type.

8. The retractor of claim 1, comprising a retention feature by which the at least one light source is removeably attached to the at least one paddle.

9. The retractor of claim 8, wherein the retention feature comprises a male runner and a female runner which receives the male runner.

10. The retractor of claim 9, wherein the male runner is disposed on the light source and the female runner is disposed on the paddle.

11. The retractor of claim 9, wherein the male runner comprises an end face which abuts a corresponding end face of the female runner.

12. The retractor of claim 8, wherein the retention feature comprises one or more male pips and one or more female slots which receive the one or more male pips.

13. The retractor of claim 8, wherein the retention feature comprises a recess in the paddle which receives the light source.

14. The retractor of claim 8, wherein the retention feature comprises one or more of studs, corresponding ridges and channels, and plugs and sockets.

15. The retractor of claim 1, wherein the second housing portion is welded to the first housing portion so as to form a hermetic seal.

16. The retractor of claim 1, wherein the LEDs are side-emitting LEDs.

17. The retractor of claim 1, wherein the first housing portion is configured, arranged or adapted to function as a waveguide which receives light from the one or more LEDs.

18. The retractor of claim 1, wherein the first housing portion comprises a diffusing surface which enables the first housing portion to function as a light guide panel.

19. The retractor of claim 18, wherein the diffusing surface comprises etching, moulding or printing on an internal face of the first housing portion.

20. The retractor of claim 1, wherein the first housing portion comprises recesses which receive the one or more LEDs to enable coupling of light into the first housing portion.

21. The retractor of claim 1, wherein the lighting module comprises a switch configured to selectively provide electrical power to the one or more LEDs.

22. The retractor of claim 21, wherein the switch comprises a press switch actuable via the first housing portion.

23. The retractor of claim 22, wherein the first housing portion comprises a dome feature aligned with the switch which actuates the switch when depressed.

24. The retractor of claim 21, wherein the switch is configured to actuate automatically when the lighting module is attached to the paddle.

25. The retractor of claim 24, wherein the switch is located on a surface of the lighting module which contacts a corresponding surface of the paddle.

26. The retractor of claim 1, comprising two paddles arranged at the ends of corresponding arms mechanically connected by a pivot which permits the retractor to be moved between a closed and an open position by handles opposing the paddles, a light source removeably attached to a distal end of each paddle by means of a retention feature comprising a male runner disposed on the light source and a corresponding female runner disposed on the paddle which receives the male runner, each light source comprising one or more side-emitting LEDs and a waveguide arranged and/or adapted to provide diffuse illumination of a workspace between the paddles.

27. A retractor light source, wherein the retractor light source comprises:
a lighting module having a first housing portion, a second housing portion attached to the first housing portion, and one or more LEDs located between the first housing portion and the second housing portion, the first housing portion comprising:
a first section and a second section wherein the first section has a thickness that is greater than that of the second section and the first section is aligned with the location of the one or more LEDs to form a light exit surface and the interface between the first section and the second section;
wherein the retractor light source is removeably attachable to a distal end of a blade of a retractor.

28. A kit of parts comprising at least one retractor comprising at least one paddle adapted, arranged or configured to receive a light source at a distal end, and at least one light source adapted as claimed in claim 27.

29. The kit of parts of claim 28 wherein the at least one light source is arranged or configured for removeable attachment to the distal end of the paddle of the at least one retractor.

30. The kit of parts of claim 29, comprising a plurality of retractors and a plurality of light sources.

* * * * *